(12) United States Patent
Kinoshita et al.

(10) Patent No.: US 9,107,687 B2
(45) Date of Patent: Aug. 18, 2015

(54) OTORHINOLARYNGOLOGICAL TREATMENT DEVICE AND METHOD

(75) Inventors: Yasushi Kinoshita, Fujinomiya (JP);
Katsuhiko Shimizu, Fujinomiya (JP);
Satoru Suehara, Ashigarakami-gun (JP); Yousuke Ootani, Shibuya-ku (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 28 days.

(21) Appl. No.: 13/432,756

(22) Filed: Mar. 28, 2012

(65) Prior Publication Data

US 2012/0253114 A1 Oct. 4, 2012

(30) Foreign Application Priority Data

Mar. 29, 2011 (JP) ................. 2011-072985

(51) Int. Cl.
*A61B 1/00* (2006.01)
*A61B 17/24* (2006.01)
(Continued)

(52) U.S. Cl.
CPC ............. *A61B 17/24* (2013.01); *A61B 1/00082* (2013.01); *A61B 1/00154* (2013.01); *A61B 1/233* (2013.01); *A61B 19/5212* (2013.01);
(Continued)

(58) Field of Classification Search
CPC ................................ A61B 1/0125; A61B 1/05
USPC ................. 600/116, 117, 104, 109; 604/529; 348/45
See application file for complete search history.

(56) References Cited

U.S. PATENT DOCUMENTS

| 5,246,420 A | * | 9/1993 | Kraus et al. ............... 604/95.01 |
| 2005/0085844 A1 | * | 4/2005 | Tremulis et al. ............ 606/193 |

(Continued)

FOREIGN PATENT DOCUMENTS

| JP | 2003-250748 A | 9/2003 |
| JP | 2007-075655 A | 3/2007 |

(Continued)

OTHER PUBLICATIONS

Written Opinion of the International Searching Authority (Form PCT/ISA/237) issued on Jun. 26, 2012, in the corresponding International Application No. PCT/JP2012/057361, and International Search Report (Form PCT/ISA/210) issued Jun. 26, 2012, in the corresponding International Application No. PCT/JP2012/057361. (9 pages).

(Continued)

*Primary Examiner* — Anhtuan T Nguyen
*Assistant Examiner* — Timothy J Neal
(74) *Attorney, Agent, or Firm* — Buchanan Ingersoll & Rooney PC

(57) ABSTRACT

A sinusitis treatment device includes: a flexible first elongated body to be guided into an accessory; an imaging unit which is provided on the first elongated long body, for obtaining an image on the front side of a distal end of the first elongated body; a flexible second elongated body having a lumen in which the first elongated body is inserted; an expansive body which is provided on the second elongated body and which has an effective expansive section capable of radial expansive deformation within a natural ostium located between a nasal cavity and an accessory nasal cavity to push open a stenosed part of the natural ostium; and a positioning unit which is provided on the second elongated body, for positioning the effective expansive section of the second elongated long body moved along the first elongated body relative to the first elongated body.

8 Claims, 16 Drawing Sheets

(51) Int. Cl.
*A61B 1/233* (2006.01)
*A61B 1/04* (2006.01)
*A61M 25/01* (2006.01)
*A61B 19/00* (2006.01)
*A61B 17/00* (2006.01)
*A61B 17/22* (2006.01)
*A61M 29/02* (2006.01)

(52) U.S. Cl.
CPC ............ *A61B2017/00557* (2013.01); *A61B 2017/22051* (2013.01); *A61B 2019/4857* (2013.01); *A61B 2019/521* (2013.01); *A61B 2019/5437* (2013.01); *A61M 25/01* (2013.01); *A61M 29/02* (2013.01)

(56) References Cited

U.S. PATENT DOCUMENTS

| | | | | |
|---|---|---|---|---|
| 2006/0004323 | A1* | 1/2006 | Chang et al. | 604/28 |
| 2006/0183975 | A1* | 8/2006 | Saadat et al. | 600/139 |
| 2007/0149951 | A1* | 6/2007 | Wu et al. | 604/526 |
| 2008/0172033 | A1 | 7/2008 | Keith et al. | |
| 2009/0312745 | A1 | 12/2009 | Goldfarb et al. | |
| 2010/0048988 | A1 | 2/2010 | Pastorelli et al. | |
| 2010/0168511 | A1 | 7/2010 | Muni et al. | |
| 2010/0274188 | A1 | 10/2010 | Chang et al. | |

FOREIGN PATENT DOCUMENTS

| | | |
|---|---|---|
| JP | 2008-049199 A | 3/2008 |
| JP | 2008-513125 A | 5/2008 |
| JP | 2009-500051 A | 1/2009 |
| JP | 2009-542268 A | 12/2009 |
| WO | 2006/104750 A1 | 10/2006 |
| WO | 2006/135853 A2 | 12/2006 |

OTHER PUBLICATIONS

Notification Concerning Transmittal of International Preliminary Report on Patentability (Form PCT/IB/326) issued on Oct. 10, 2013 by the Japanese Patent Office for International Application No. PCT/JP2012/057361. (7 pages).

Notification of Transmittal of Translation of the International Preliminary Report on Patentability (Form PCT/IB/338) issued on Oct. 10, 2013 by the Japanese Patent Office for International Application No. PCT/JP2012/057361. (7 pages).

European Search Report dated Jul. 18, 2014 for corresponding Application No. 12765961.3.

* cited by examiner

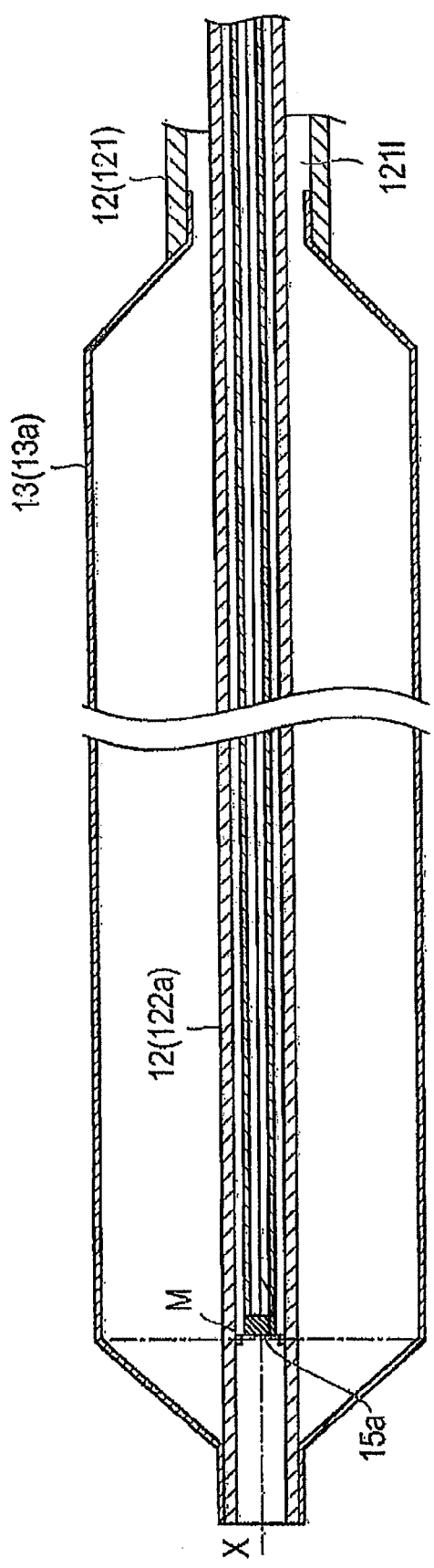

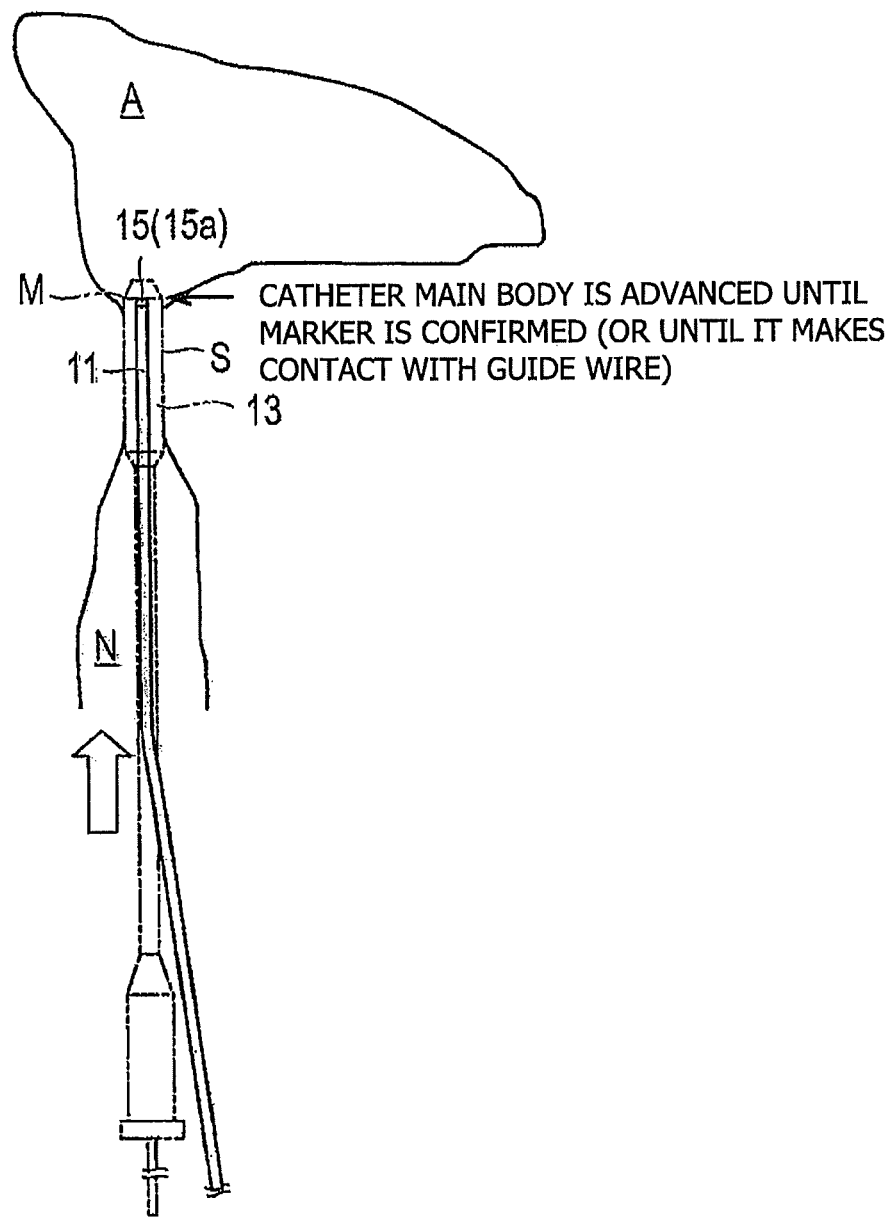

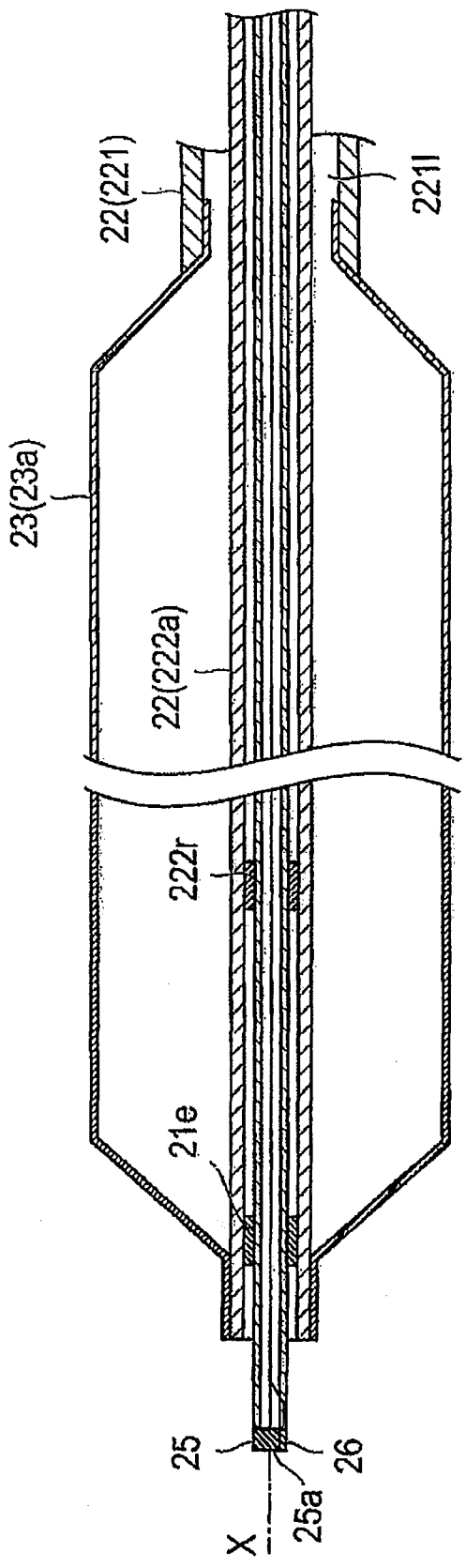

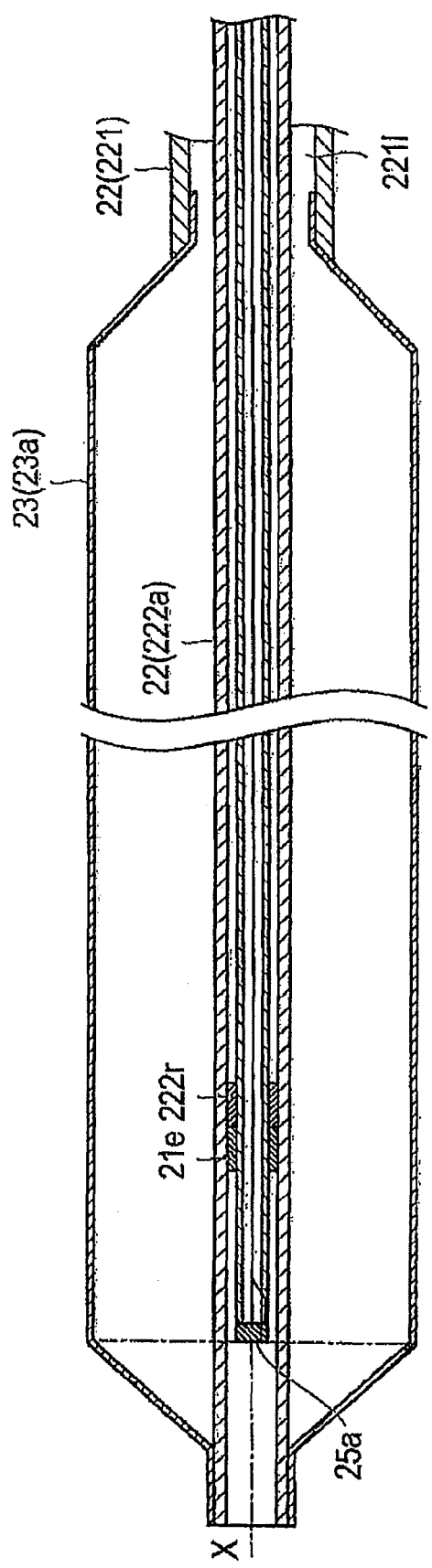

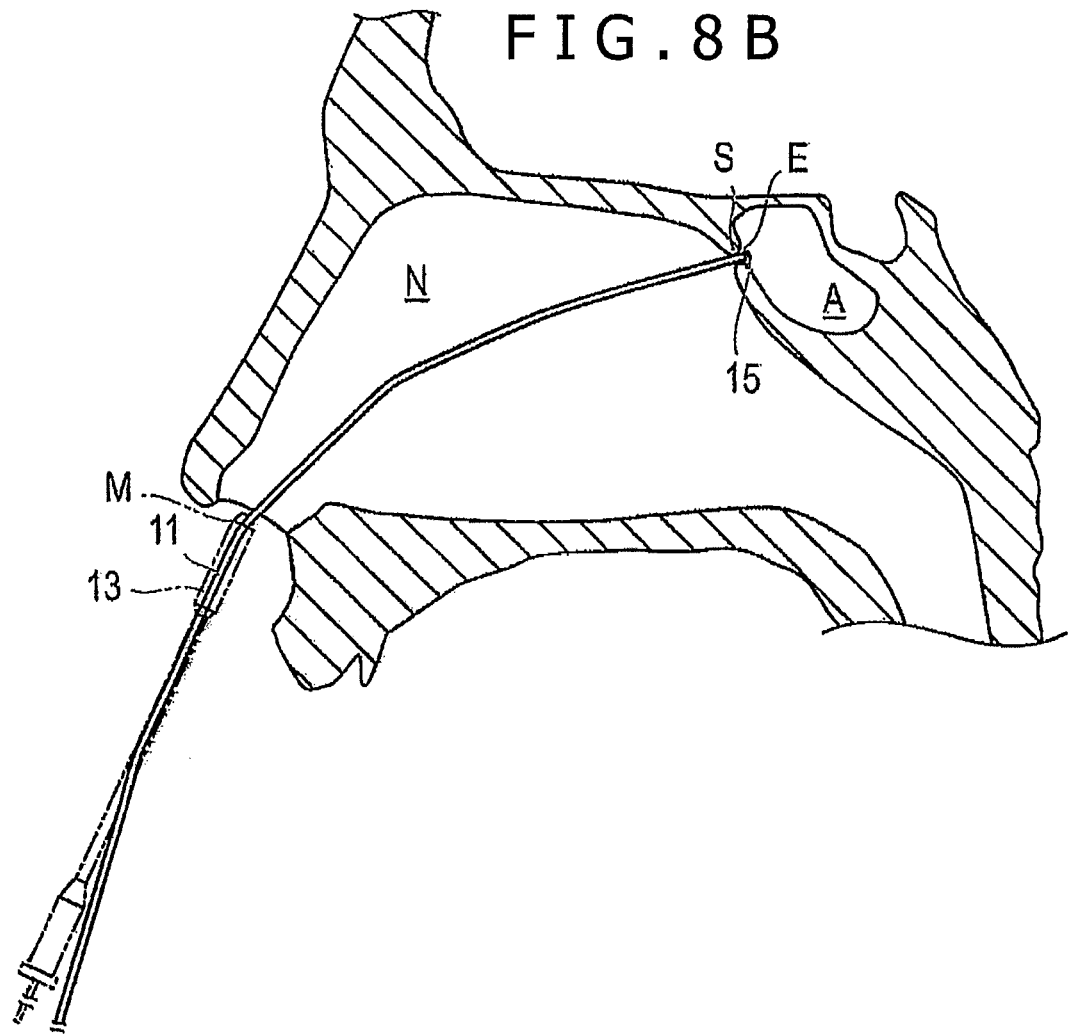

CATHETER MAIN BODY IS ADVANCED UNTIL MARKER IS CONFIRMED (OR UNTIL IT MAKES CONTACT WITH GUIDE WIRE)

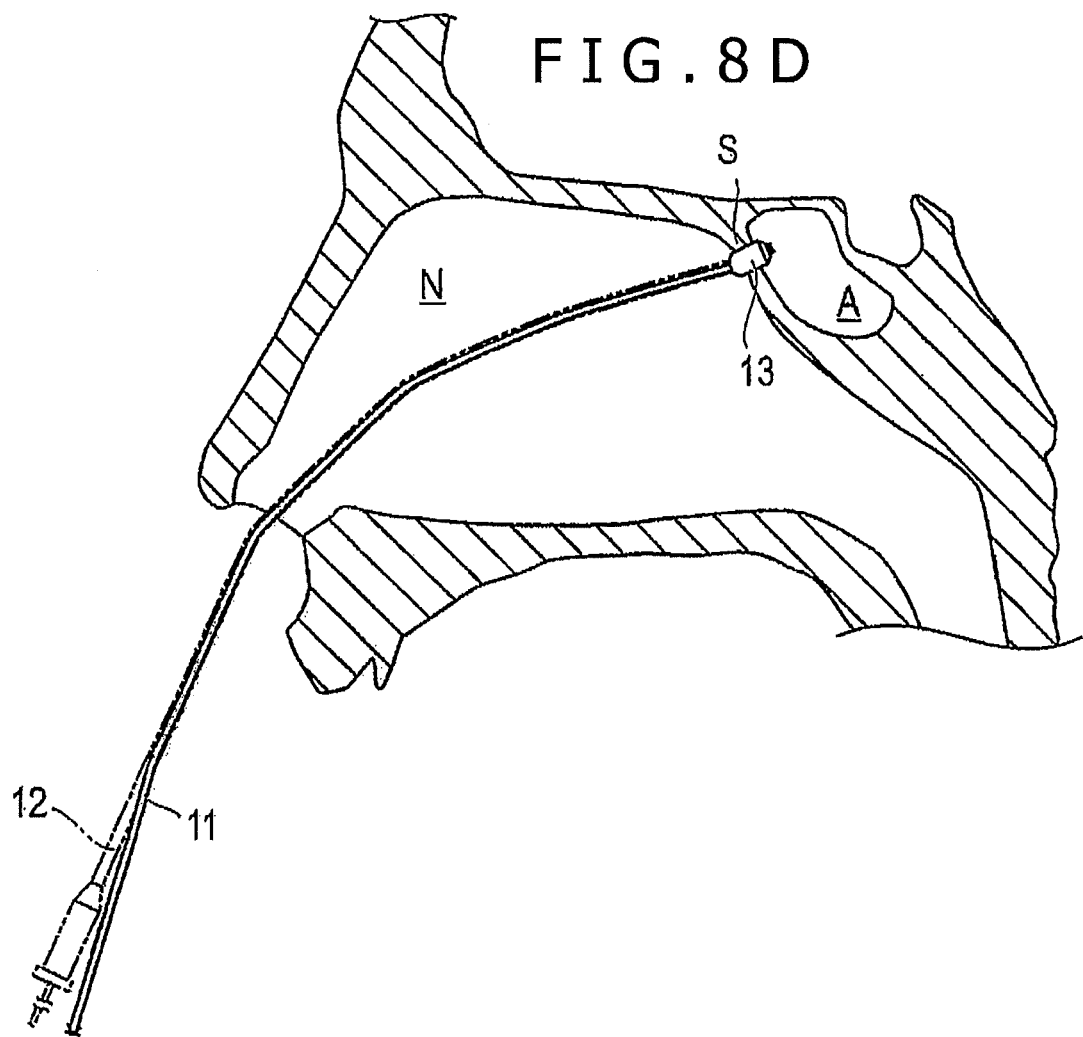

OTORHINOLARYNGOLOGICAL TREATMENT DEVICE AND METHOD

CROSS-REFERENCE TO RELATED APPLICATION

This application is based upon and claims the benefits of priority from the prior Japanese Patent Application No. 2011-072985 filed on Mar. 29, 2011, the entire contents of which are incorporated herein by reference.

BACKGROUND

1. Technical Field

The present invention relates to an otorhinolaryngological treatment device to be used for treatment of sinusitis or the like and an otorhinolaryngological treatment method thereof.

2. Description of Related Art

An accessory nasal cavity is an intraosseous cavity adjacent to a nasal cavity, and communicates with the nasal cavity through a small hole called natural ostium. Secretions, bacteria and the like in the accessory nasal cavity are excreted into the nasal cavity through the natural ostium. When the mucous membrane in the nasal cavity is swollen due to common cold-induced rhinitis or allergic rhinitis or the like or the inside of the nasal cavity is narrowed due to deflected nasal septum or hypertrophic rhinitis or the like, however, the natural ostium is stenosed and chronic inflammation is generated in the accessory nasal cavity. Such a disease is called sinusitis. Conventionally, the method for treatment of sinusitis has generally been a surgical operation in which the lesion causing stenosis of the natural ostium is removed by use of forceps, a drill or the like while confirming the video image of the inside of the nasal cavity through an endoscope. In recent years, however, a sinusitis treatment method based on the use of a balloon catheter and not including a surgical operation has been developed, and has been drawing attention from the viewpoint of minimal invasiveness to the patient.

In the treatment method developed recently, a guide wire and a balloon catheter are sequentially inserted into the nasal cavity, and, after it is radioscopically confirmed that the balloon catheter has been disposed in the natural ostium, the balloon catheter is expanded to force open the stenosed part of the natural ostium. According to this treatment method, the communicating passage between the nasal cavity and the accessory nasal cavity can be recovered while greatly alleviating the bleeding in the nasal cavity, damage to the mucous membrane, etc. In connection with this technique, Japanese Patent Application Publication No. 2008-513125 proposes a balloon catheter in which a plurality of radiopaque markers for marking the balloon proximal end, distal end and the like are disposed on the inner surface of the balloon. On the other hand, from the viewpoint of prevention of exposure of the patient to X-rays, there is an increasing demand for a balloon catheter which enables easy positioning of the balloon inside the nasal cavity without relying on radioscopy.

SUMMARY

The present invention has been made aiming at solving the above-mentioned problem involved in the related art. Accordingly, it is an object of the present invention to provide an otorhinolaryngological treatment device in which positioning of an expansion body inside a nasal cavity can be easily carried out without need for radioscopy.

A first mode of the present invention provides an otorhinolaryngological treatment device including: a flexible first elongated body; an imaging unit which is provided on the first elongated body, for obtaining an image on the front side of a distal end of the first elongated body; a flexible second elongated body having a lumen in which the first elongated body is inserted; an expansive body which is provided on the second elongated body and has an effective expansive section capable of radial expansive deformation within a natural ostium located between a nasal cavity and an accessory nasal cavity to push open a stenosed part of the natural ostium; and a positioning unit which is provided on the second elongated body, for positioning the effective expansive section of the second elongated body moved along the first elongated body relative to the first elongated body.

In the treatment device, the positioning unit may have a marker which is disposed on the second elongated body and which can be visually confirmed in the image obtained by the imaging unit.

In the treatment device, the marker may be a recess or projection which is disposed on the second elongated body.

In the treatment device, the marker may be a boundary line between different colors on the second elongated body.

In the treatment device, the marker may be disposed on an inner circumferential surface of the lumen in such a manner that positions of the effective expansive section and the marker projected onto an extension axis of the second elongated body coincide with each other.

In the treatment device, the positioning unit may have a contact section which is disposed on the inner circumferential surface of the lumen and which makes contact with the first elongated body when the second elongated body is moved along the first elongated body.

In the treatment device, the first elongated body may have an enlarged diameter section which is partially enlarged in a radial direction, and the contact section makes contact with the enlarged diameter section of the first elongated body.

In the treatment device, the contact section may be disposed on the inner circumferential surface of the lumen in such a manner that positions of the effective expansive section and an image obtaining plane of the imaging unit projected onto an extension axis of the second elongated body coincide with each other when the contact section makes contact with the first elongated body.

In the treatment device, the imaging unit may be located at a distal end of the first elongated body.

A second mode of the present invention provides a method of dilating a stenosed part of a natural ostium of an accessory nasal cavity, including steps of: inserting a flexible first elongated body which is inserted in a lumen of a flexible second elongated body having an expansion body and which has an imaging unit, into the accessory nasal cavity on the basis of an image obtained by the imaging unit; advancing the second elongated body along the first elongated body thereby to introduce the second elongated body into the accessory nasal cavity; positioning and disposing an effective expansive section of the expansion body in the stenosed part by means of a positioning unit provided on the second elongated body; and expanding the expansion body to push open the stenosed part.

In the method of dilating a stenosed part, the positioning unit may have a marker which is disposed on the second elongated body and which can be visually confirmed in the image obtained by the imaging unit; and the step of disposing the effective expansive section in the stenosed part includes a step of confirming the position of the marker through the imaging unit.

In the method of dilating a stenosed part, the positioning unit may have a contact section which is disposed on the inner circumferential surface of the lumen and which makes contact with the first elongated body when the second elongated body is moved along the first elongated body; and the step of disposing the effective expansive section in the stenosed part includes a step of confirming the position of the contact section by bringing the contact section into contact with the first elongated body.

In the method of dilating a stenosed part, the step of pushing open the stenosed part may include a step of expanding and contracting the expansion body while advancing or retreating the second elongated body in a living body.

According to the first mode of the invention, by delivering the first elongated body into the accessory nasal cavity while watching the image obtained by the imaging unit, and then positioning the second elongated body moved along the first elongated body relative to the first elongated body by the positioning unit, the expansion body provided on the second elongated body can be positioned accurately in the stenosed part of the natural ostium. According to this invention, therefore, the stenosed part of the natural ostium can be securely pushed open by the expansion body, so that a therapeutic effect on sinusitis can be enhanced. According to this invention, further, the first elongated body and the second elongated body can be prevented from being advanced excessively into the accessory nasal cavity, so that safety in treatment of sinusitis can be enhanced. In addition, according to this invention, there is no need for a large-scale special apparatus such as a fluoroscopic apparatus, and treatment of sinusitis can be carried out by use of an endoscope or the like equipped in many hospitals.

According to this invention, by delivering the first elongated body into the accessory nasal cavity while watching the image obtained by the imaging unit, and then advancing the second elongated body along the first elongated long body until the marker is visually confirmed in the image obtained by the imaging unit, the expansion body provided on the second elongated body can be positioned accurately in the stenosed part of the natural ostium. According to this invention, therefore, the stenosed part of the natural ostium can be assuredly pushed open, so that a therapeutic effect on sinusitis can be enhanced.

According to this invention, by delivering the first elongated body into the accessory nasal cavity while watching the image obtained by the imaging unit, and then advancing the second elongated body along the first elongated body until the marker (recess or projection) is visually confirmed in the image obtained by the imaging unit, the expansion body provided on the second elongated body can be positioned accurately in the stenosed part of the natural ostium. According to this invention, therefore, the stenosed part of the natural ostium can be securely pushed open, so that a therapeutic effect on sinusitis can be enhanced.

According to this invention, by delivering the first elongated body into the accessory nasal cavity while watching the image obtained by the imaging unit, and then advancing the second elongated body along the first elongated body until the marker (the boundary of different colors) is visually confirmed in the image obtained by the imaging unit, the expansion body provided on the second elongated body can be positioned accurately in the stenosed part of the natural ostium. According to this invention, therefore, the stenosed part of the natural ostium can be pushed open assuredly, so that a therapeutic effect on sinusitis can be enhanced.

According to this invention, by delivering the first elongated body into the accessory nasal cavity while watching the image obtained by the imaging unit, and then advancing the second elongated body along the first elongated body until the marker is visually confirmed in the image obtained by the imaging unit, the effective expansive section of the expansion body can be positioned substantially in the whole of the stenosed part. According to this invention, therefore, the stenosed part of the natural ostium can be pushed open more assuredly, so that a therapeutic effect on sinusitis can be further enhanced.

According to this invention, by delivering the first elongated body into the accessory nasal cavity while watching the image obtained by the imaging unit, and then advancing the second elongated body along the first elongated body until the contact section is brought into contact with the first elongated body, the expansion body provided on the second elongated body can be positioned accurately in the stenosed part of the natural ostium. According to this invention, therefore, the stenosed part of the natural ostium can be pushed open securely, so that a therapeutic effect on sinusitis can be enhanced.

According to this invention, by delivering the first long body into the accessory nasal cavity while monitoring the image obtained by the imaging unit, and then advancing the second elongated body along the first elongated body until the contact section is brought into contact with the enlarged diameter section of the first elongated body, the expansion body provided on the second elongated body can be positioned accurately in the stenosed part of the natural ostium. According to this invention, therefore, the stenosed part of the natural ostium can be pushed open assuredly, so that a therapeutic effect on sinusitis can be enhanced.

According to this invention, by delivering the first elongated body into the accessory nasal cavity while watching the image obtained by the imaging unit, and then advancing the second elongated body along the first elongated body until the contact section is brought into contact with the first elongated body, the effective expansive section of the expansion body can be positioned in substantially the whole of the stenosed part. According to this invention, therefore, the stenosed part of the natural ostium can be pushed open more securely, so that a therapeutic effect on sinusitis can be further enhanced.

According to this invention, the image obtaining plane is always located at the distal end of the pathway of the first elongated body, and hence the arrival of the first elongated body at the accessory nasal cavity can be confirmed more accurately. According to this invention, therefore, a therapeutic effect on sinusitis and safety in treatment of sinusitis can be further enhanced.

According to the second mode of the invention, by delivering the first elongated body into the accessory nasal cavity while watching the image obtained by the imaging unit, and then positioning the second elongated body moved along the first elongated body relative to the first elongated body by means of the positioning unit, the expansion body provided on the second elongated body can be positioned accurately in the stenosed part of the natural ostium. According to this invention, therefore, the stenosed part of the natural ostium can be pushed open more assuredly by the expansion body, so that a therapeutic effect on sinusitis can be enhanced. According to this invention, further, the first elongated body and the second elongated body can be prevented from being advanced excessively into the accessory nasal cavity, so that safety in treatment of sinusitis can be enhanced. In addition, according to this invention, there is no need for a large-scale special apparatus such as a fluoroscopic apparatus, and treatment of sinusitis can be carried out by an endoscope or the like equipped in many hospitals.

According to this invention, by delivering the first elongated body into the accessory nasal cavity while watching the image obtained by the imaging unit, and then advancing the second elongated body along the first elongated body until the marker is visually confirmed in the image obtained by the imaging unit, the expansion body provided on the second elongated body can be positioned accurately in the stenosed part of the natural ostium. According to this invention, therefore, the stenosed part of the natural ostium can be pushed open assuredly, so that a therapeutic effect on sinusitis can be enhanced.

According to this invention, by delivering the first elongated body into the accessory nasal cavity while watching the image obtained by the imaging unit, and then advancing the second elongated body along the first elongated body until the contact section is brought into contact with the first elongated, the expansion body provided on the second elongated body can be positioned accurately in the stenosed part of the natural ostium. According to this invention, therefore, the stenosed part of the natural ostium can be pushed open securely, so that a therapeutic effect on sinusitis can be enhanced.

According to this invention, by expanding and contracting the expansion body while advancing or retreating the second elongated body in a living body, the stenosed part of the natural ostium can be pushed open more assuredly.

BRIEF DESCRIPTION OF THE DRAWINGS

FIG. 5B is a longitudinal sectional view showing the vicinity of an effective expansive section of the balloon of the catheter of FIG. 2;

FIG. 6B is a schematic view showing a positioning method of a catheter according to another embodiment of the present invention;

FIG. 7A is a schematic view showing a positioning method of a catheter according to another embodiment of the present invention;

FIG. 7B is a schematic view showing a positioning method for a catheter according to another embodiment of the present invention;

FIG. 8B is a schematic view showing a sinusitis treatment method using a treatment device according to one embodiment of the present invention;

FIG. 8D is a schematic view showing a sinusitis treatment method using a treatment device according to one embodiment of the present invention;

DETAILED DESCRIPTION OF THE PREFERRED EMBODIMENTS

Figure 1:
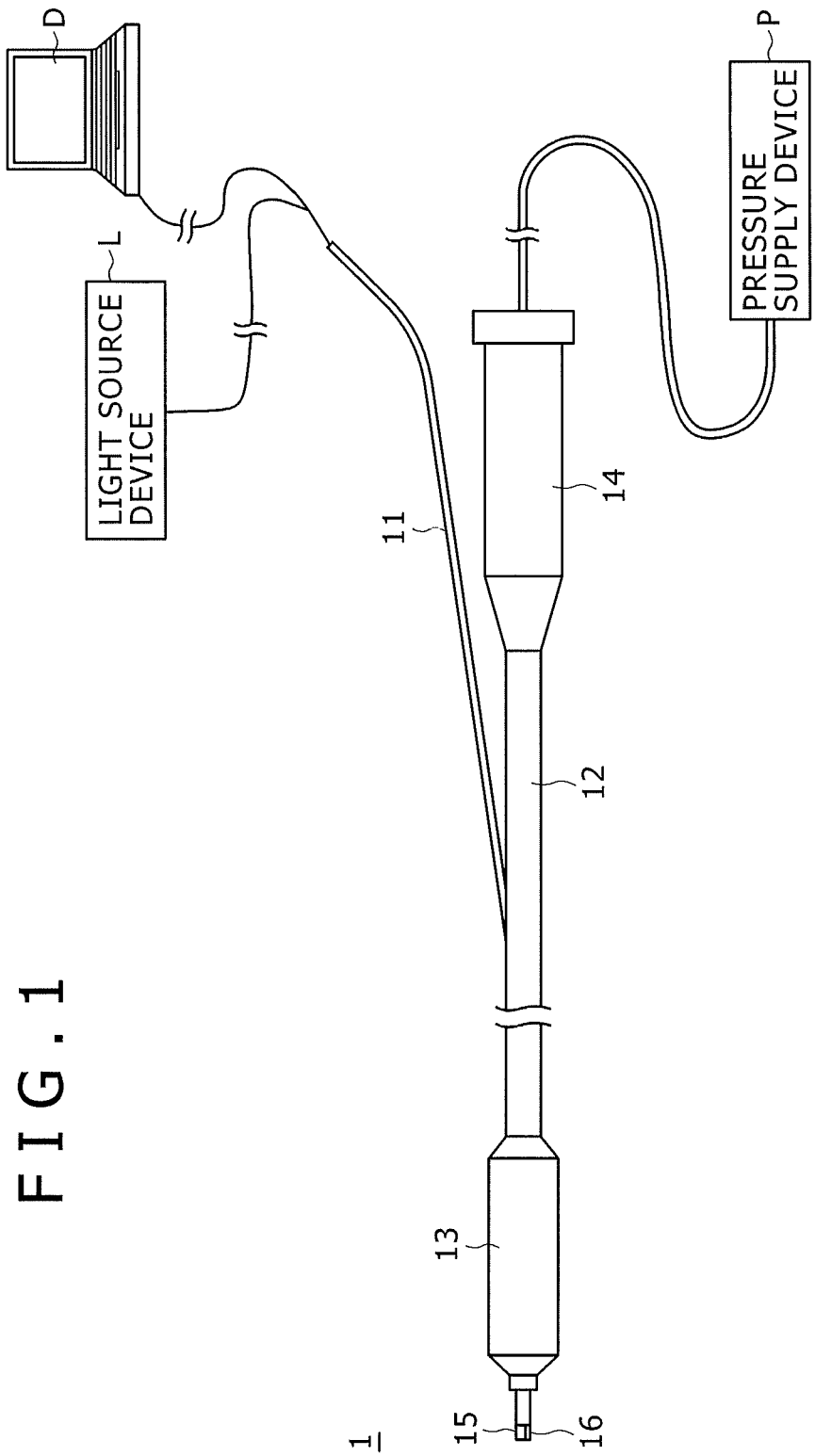
FIG. 1 is a schematic view of the entire structure of a treatment system including a treatment device (catheter) according to one embodiment of the present invention.

Now, embodiments of the present invention will be described below referring to the drawings. Incidentally, for convenience of description, the dimensional ratios among components in each of the drawings as well as the dimensional ratios of the same components among the plurality of drawings are modified as required, so that they are not necessarily coincident with the actual ratios.

<Structure of Treatment Device According to the Present Invention>

FIG. 1 is a schematic view showing the general structure of a treatment system including a catheter 1 as a treatment device according to a first embodiment of the present invention. As shown in FIG. 1, the catheter 1 includes a first elongated body 11 having a function as a guide wire for guiding a catheter main body to a desired part in a nasal cavity, a second elongated body 12 having a function as the catheter main body to be guided by the first elongated body, a balloon 13 having a function as an expansion body for pushing open a stenosed part of a natural ostium of the nasal cavity, and a hub 14 having a function as a proximal operating section to be operated by the operator.

The catheter 1 is inserted into a patient's nasal cavity from its end portion on the left side in FIG. 1, to be used for treatment of sinusitis. In the following description, the end portion of the catheter 1 for insertion into the nasal cavity will be referred to as the "distal end," and the end portion on the opposite side as the "proximal end." As shown in FIG. 1, the catheter 1 is a so-called "rapid exchange" type catheter in which a guide wire is inserted in only the vicinity of the distal end of a catheter main body. It is to be noted, however, that the form of the catheter 1 is not restricted to the example shown in FIG. 1. Thus, the catheter 1 may be a so-called "over-the-wire" type catheter in which a guide wire is inserted in substantially the whole length of a catheter main body.

As shown in FIG. 1, the first elongated body 11 is provided with a CCD camera 15 having a function as an imaging unit for obtaining an image on the inside of a nasal cavity, and an LED light 16 having a function as a lighting unit for illuminating the inside of the nasal cavity in order to secure a visual field for the CCD camera 15. The CCD camera 15 has an image obtaining plane substantially orthogonal to an extension axis of the first elongated body 11, so that an image of the inside of the patient's nasal cavity can be thereby obtained when the first elongated body 11 is inserted into the nasal cavity. In addition, the LED light 16 is preferably disposed in parallel to the CCD camera 15 so as to be capable of illuminating the front side of the image obtaining plane of the CCD camera 15. The CCD camera 15 and the LED light 16 are preferably attached to the distal end of the first elongated body 11 so that an accurate image of the inside of the nasal cavity can be obtained.

The "CCD camera" here means a digital video camera using a CCD image sensor as an imaging element. It should be noted here, however, that the imaging unit in the present embodiment is not restricted only to the CCD camera but may be any of a digital video camera using other imaging element such as a CMOS image sensor, an image fiber for obtaining and transmitting images through the use of optical fibers, and an imaging system for transmitting images by means of an objective lens and an optical system including a plurality of relay lenses. In addition, the lighting unit in the present embodiment is not limited only to the LED light, but may be other lighting units such as a halogen lamp and a high-intensity discharge lamp (HID lamp). Apart from the example shown in FIG. 1 where the LED lamp L is attached to the distal end of the first elongated body 11, the first elongated body 11 can also be configured such that light generated by a light source device (described later) is guided to its distal end through a light guide made by glass or plastic.

As shown in FIG. 1, connection cables for connecting the CCD camera 15 and the LED light 16 with a display device D and a light source device L, respectively, are led out from the proximal end of the first elongated body 11. In other words, the connection cables are disposed in the lumen of the first elongated body 11. In addition, a connection tube for connecting the hub 14 with a pressure supply device P is led out from a pressure supply port 14a provided at the proximal end of the hub 14. Here, the display device D is a display, such as an LCD, for displaying the image obtained by the CCD camera 15. The light source device L is a power source device for supplying electric power to the LED light 14. The pressure supply device P is a pressure supply device, such as an indeflator, for supplying a liquid or the like for inflating the balloon 13.

Figure 2:
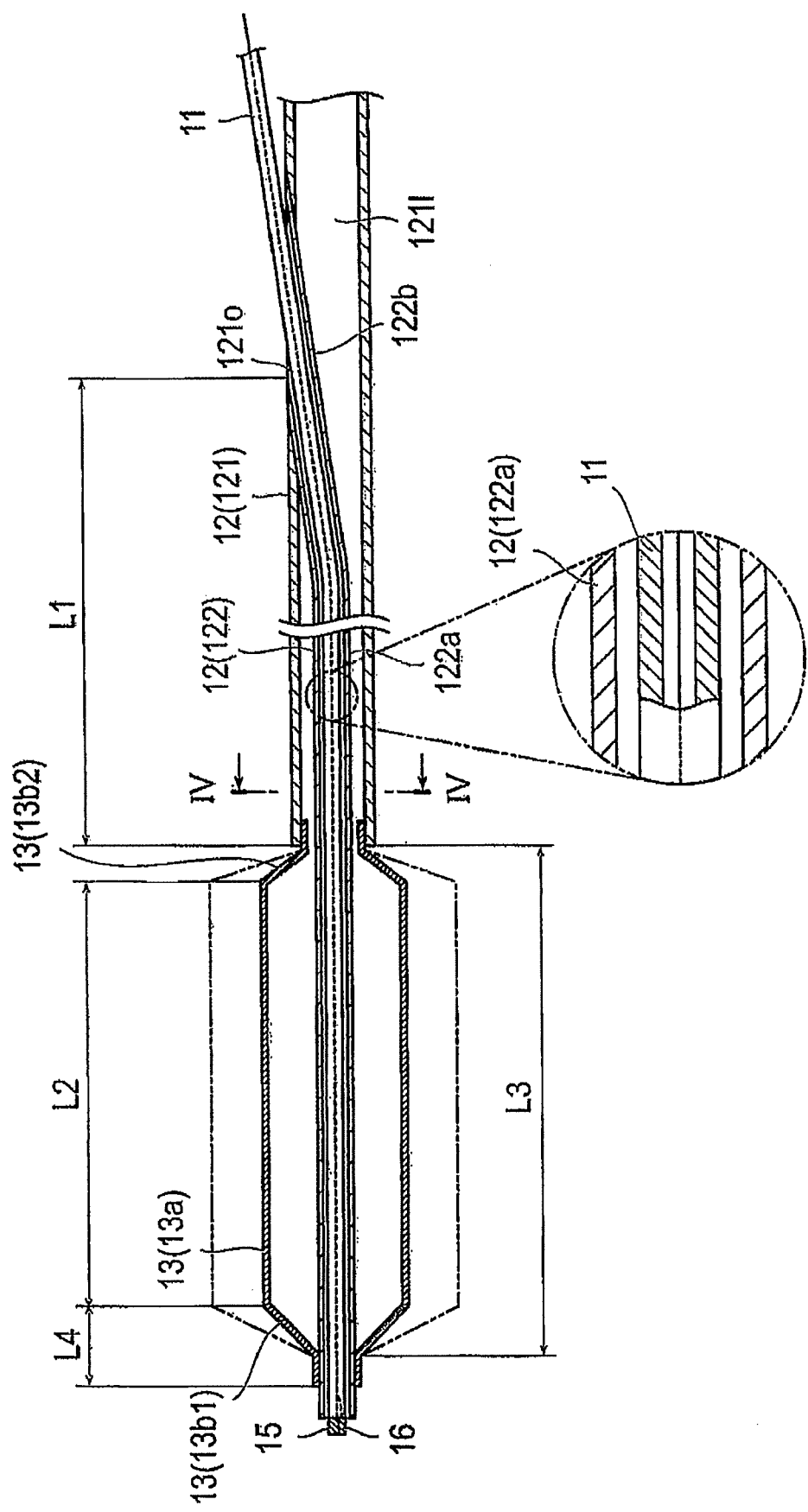
FIG. 2 is an enlarged longitudinal sectional view showing a major part of the catheter of FIG. 1.

FIG. 2 is an enlarged longitudinal sectional view showing a major part of the catheter 1 of FIG. 1. As shown in FIG. 2, the first elongated body 11 is inserted in a lumen of an inner tube 122 (described later) of the second elongated body 12. In addition, of the first elongated body 11, the distal end is led out to the exterior from the distal end of the second elongated body 12, and the proximal end is led out to the exterior from an opening part 1210 provided in an outer circumferential surface of the second elongated body 12. Such a configuration ensures that the first elongated body 11 can be advanced into the patient's nasal cavity by moving along the lumen of the second elongated body 12 which is fixed. Similarly, the second elongated body 12 can be advanced into the patient's nasal cavity by moving along the first elongated body 11 which is fixed to the patient's nasal cavity. Incidentally, as above-mentioned, the CCD camera 15 and the LED light 16 are attached to the distal end of the first elongated body 11, and the connection cables for the CCD camera 15 and the LED light 16 are disposed in the lumen of the first elongated body 11.

As shown in FIG. 2, the second elongated body 12 has a double-tube structure composed of an outer tube 121 and an inner tube 122, wherein the distal portion of the inner tube 122 protrudes by a predetermined length from the distal portion of the outer tube 121. In addition, the inner tube 122 includes a distal-side parallel section 122a parallel to the outer tube 121, and a proximal-side inclined section 122b having a predetermined inclination angle ("θ" in FIG. 2) relative to the outer tube 121. As shown in FIG. 2, the proximal end of the inclined section 122b is fitted, in a gas-tight manner, to the opening part 121o provided in the outer tube 121. Therefore, a liquid or the like injected into a lumen 1211 of the outer tube 121 is prevented from leaking out to the exterior through the opening part 121o.

As shown in FIG. 2, the balloon 13 has a straight barrel-like effective expansive section 13a which is substantially parallel to the outer tube 121 and the parallel section 122a, and tapered sections 13b1 and 13b2 disposed respectively on both sides of the effective expansive section 13a so that the effective expansive section 13a is located between them. In addition, the tapered section 13b1 on the distal side is joined at its distal end to an outer circumferential surface of the parallel section 122a in a gas-tight manner, whereas the tapered section 13b2 on the proximal side is joined at its proximal end to an inner circumferential surface of the outer tube 121. Therefore, a liquid or the like injected into the lumen 1211 of the outer tube 121 is prevented from leaking out to the exterior via any of the joint parts of the tapered sections 13b1 and 13b2.

Figure 3:
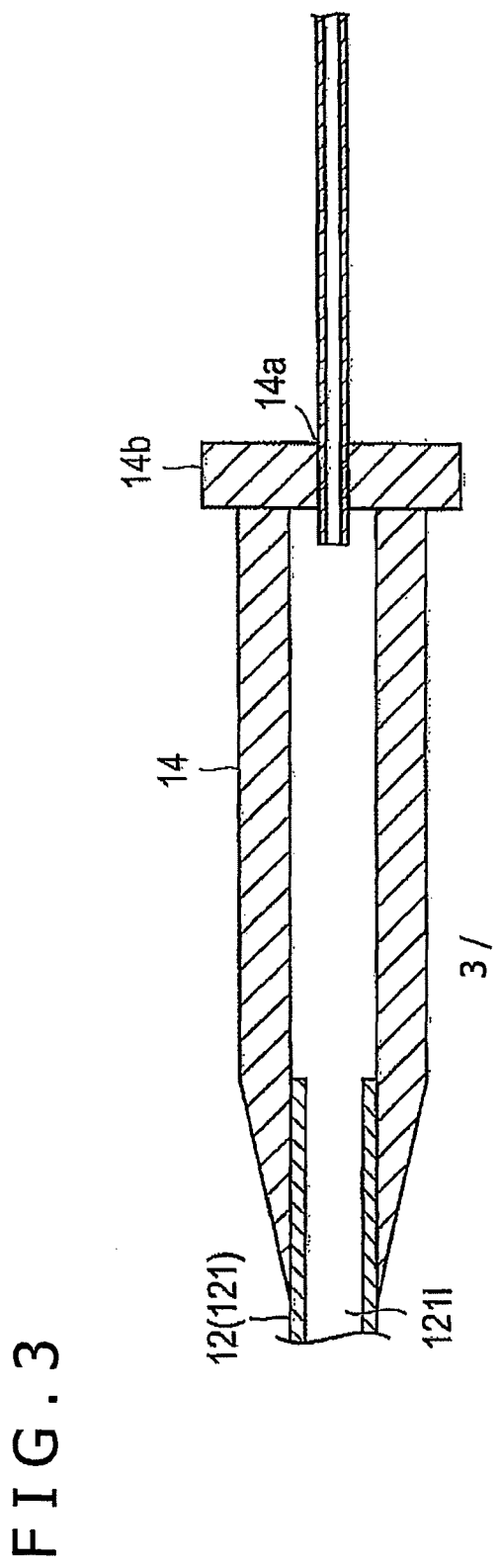
FIG. 3 is an enlarged longitudinal sectional view showing the vicinity of a hub of the catheter of FIG. 1.

FIG. 3 is an enlarged longitudinal sectional view showing the vicinity of the hub 14 of the catheter 1 of FIG. 1. As shown in FIG. 3, the vicinity of the proximal end of the outer tube 121 is fitted in the hub 14 in a gas-tight manner, and the lumen 1211 of the outer tube 121 communicates with an inside space of the hub 14. In addition, an end wall 14b sealing the proximal side of the hub 14 in a gas-tight manner is provided at the proximal end of the hub 14, and the end wall 14b is formed with the above-mentioned pressure supply port 14a. Besides, the connection tube for connection with the pressure supply device P as above-mentioned is fitted in the pressure supply port 14a. Therefore, a liquid or the like injected into the lumen 1211 of the outer tube 121 is prevented from leaking out to the exterior through the proximal end of the outer tube 121 or the proximal end of the hub 14.

As above-mentioned, the lumen 1211 (the part exclusive of the inner tube 122) of the outer tube 121 forms a fluid passage through which the inside space of the hub 14 and the inside space of the balloon 13 communicate with each other. In other words, a liquid or the like injected from the pressure supply device P into the inside space of the hub 14 through the pressure supply port 14a passes through the fluid passage, to be injected into the inside space of the balloon 13. By the liquid or the like injected in this manner, the balloon 13 is inflated in the radial direction of the effective expansive section 13a, and, at the outer circumferential surface of the effective expansive section 13a, it presses the inner circumferential surface of the stenosed part, thereby pushing open the stenosed part. This point will be further described later. The broken line in FIG. 2 represents the outside diameter of the balloon 13 in the inflated state (the same applies also in FIG. 4). Incidentally, the pressure of the liquid or the like supplied by the pressure supply device P in the present embodiment is preferably 1 to 30 atm.

Figure 4:
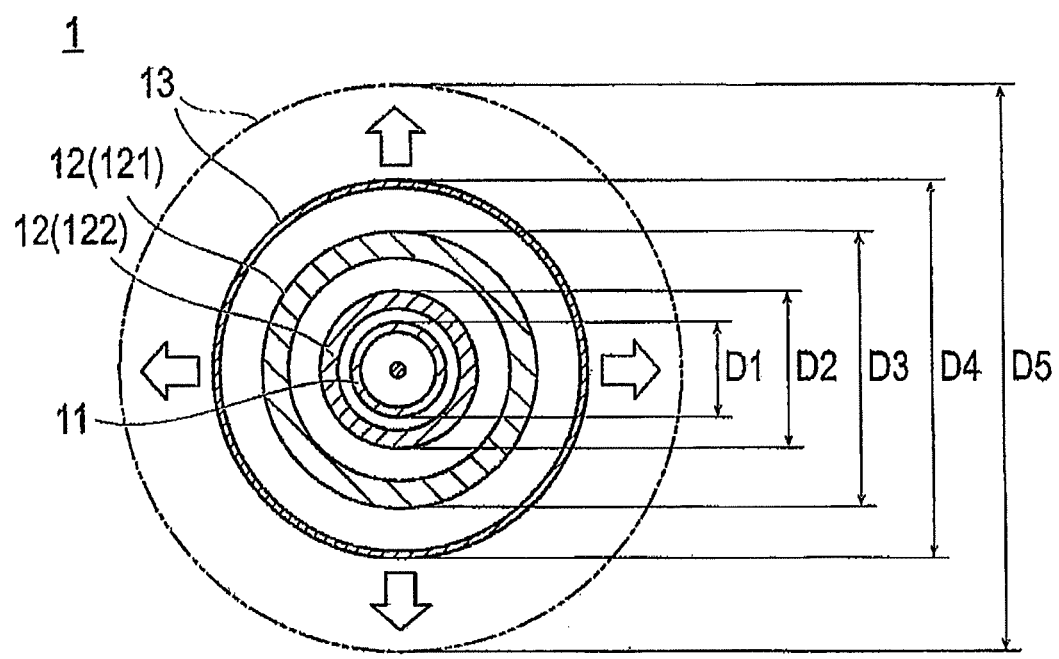
FIG. 4 is a cross-sectional view along line IV-IV of FIG. 2.

FIG. 4 is a cross-sectional view along line IV-IV of FIG. 2. As shown in FIG. 4, the center position in the radial direction of the outer tube 121 of the second elongated body 12 and the center position in the radial direction of the balloon 13 are preferably disposed coaxially. This ensures that penetrability of the balloon 13 into the nasal cavity before inflation can be enhanced.

Figure 5A:
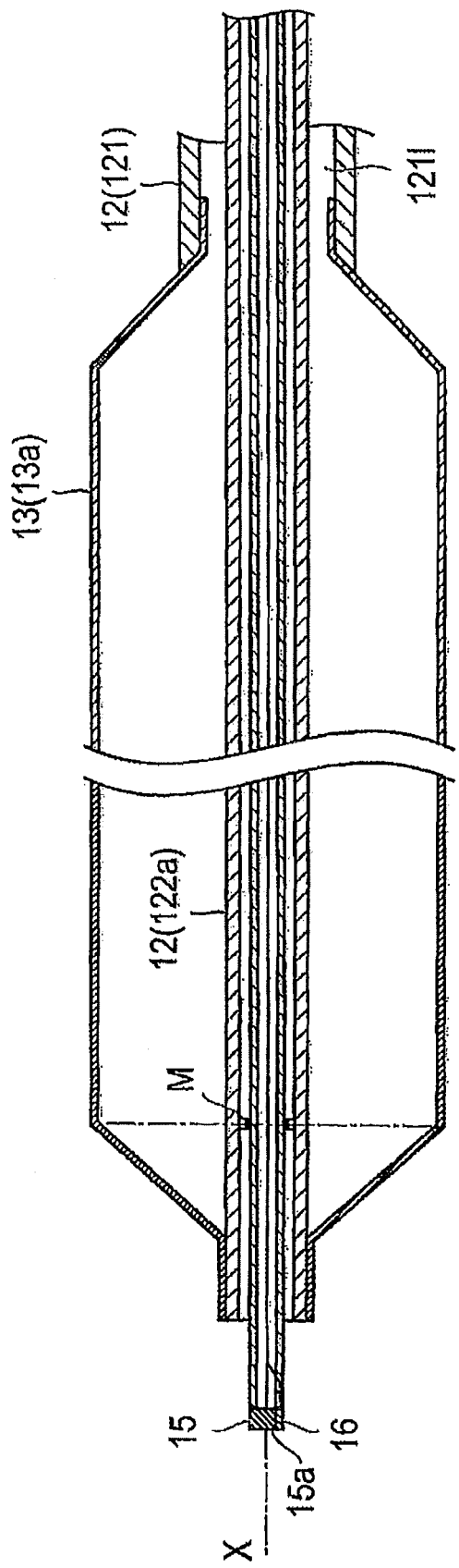
FIG. 5A is a longitudinal sectional view showing the vicinity of an effective expansive section of a balloon of the catheter of FIG. 2.

FIG. 5A is a further enlarged longitudinal sectional view showing the vicinity of the balloon 13 in FIG. 2. As shown in FIG. 5A, the second elongated body 12 is equipped with a positioning unit for positioning the balloon 13 (the effective expansive section 13a) relative to the first elongated body 11. More specifically, the positioning unit in the present embodiment is a marker M which becomes visually observable in the image obtained by the CCD camera 15 upon arrival on the front side of the image obtaining plane 15a by moving along the first elongated body, and which is disposed on the inner circumferential surface of the parallel section 122a of the inner tube 122.

As shown in FIG. 5A, the marker M is preferably so disposed that the position of projection thereof onto the extension axis of the parallel section 122a coincides with that of the effective expansive section 13a, and is particularly preferably so disposed that its projected position onto the extension axis of the parallel section 122a coincides with that of the distal end of the effective expansive section 13a. Incidentally, the extension axis of the parallel section 122a will hereinafter be referred to as "X-axis." While the marker M in the example shown in FIG. 5A is a straight line drawn on the inner circumferential surface of the parallel section 122a, it may be a straight line drawn on the outer circumferential surface of the parallel section 122a in the case where the parallel section 122a is formed from a transparent material. While the color of the marker M is not specifically restricted, it is preferably a color which has high brightness and high chroma and which can be visually confirmed with ease in the image obtained by the CCD camera 15. In addition, where the color of the marker M is a fluorescent color, its visibility can be further enhanced.

The method for forming the marker M on the parallel section 122a is not particularly restricted. In the case where the marker M is a straight line or the like drawn on the parallel section 122a as shown in FIG. 5A, the marker M may be formed by printing the straight line or the like directly on the inner circumferential surface or the outer circumferential surface of the parallel section 122a, or may be formed by a method in which a transparent film with the straight line or the like preliminarily printed thereon is adhered to the inner circumferential surface or the outer circumferential surface of the parallel section 122a by use of a transparent adhesive.

Incidentally, the form of the marker M is not restricted to the straight line drawn on the parallel section 122a as shown in FIG. 5A, but may be a symbol or pattern or the like drawn on the parallel section 122a. In addition, the marker M may be a boundary line between different colors that is formed by a method in which the color of the inner circumferential surface, the outer circumferential surface or the whole of the parallel section 122a is varied at a predetermined position along the X-axis. Furthermore, instead of the marker M consisting of the straight line or the like drawn on the inner circumferential surface of the parallel section 122a as shown in FIG. 5A, a marker M may be adopted which consists of a recess or a projection or the like mechanically formed at the inner circumferential surface of the parallel section 122a.

FIG. 5B is a longitudinal sectional view showing a condition where the positional relationship of the second elongated body 12 relative to the first elongated body 11 in FIG. 5A has been changed. As shown in FIG. 5B, the marker M on the second elongated body 12 moved along the first elongated body 11 becomes visually confirmable in the image obtained by the CCD camera 15 upon arrival at the front side of the image obtaining plane 15a. In other words, when the second elongated body 12 is stopped upon visual confirmation of the marker M in the image obtained by the CCD camera 15, the projected positions of the distal end of the effective expansive section 13a and the image obtaining plane 15a of the CCD camera 15 onto the X-axis can be made to coincide with each other as shown in FIG. 5B. This point will be further described later.

Now, materials for various parts of the catheter 1 will be described below. First, the material for the first elongated body 11 (guide wire) will be described. The first elongated body 11 is formed from one of various resin materials which are commonly used in the field of medical catheters. It is necessary for the material, however, to have such a degree of flexibility that the first elongated body 11 will not damage the mucous membrane in the periphery thereof when inserted into the nasal cavity and that the first elongated body 11 will be freely bent according to the pressures exerted from the nasal cavity inside walls. More specifically, examples of the material which can be adopted for the first elongated body 11 include resins such as polyolefins such as polyethylene, polypropylene, ethylene-propylene copolymer, ethylene-vinyl acetate copolymer, and their crosslinked products and partially crosslinked products (e.g., crosslinked ethylene-vinyl acetate copolymer), etc., polyvinyl chloride, nylon elastomers, fluorine resins, polyurethane, etc., and rubbers such as silicone rubbers, latex rubbers, etc.

Besides, it is also necessary for the outer tube 121 and the inner tube 122 of the second elongated body 12 to have such a degree of flexibility that they will not damage the mucous membrane in the peripheries thereof when inserted into the nasal cavity and that they will be freely bent according to the pressures exerted from the nasal cavity inside walls. These members are formed from one of materials which are the same as or similar to the materials for the first elongated body 11. The first elongated body 11 and the second elongated body 12 may be formed from the same material or formed from different materials.

Now, the material for the balloon 13 will be described. The balloon 13 is formed from one of various resin materials which are commonly used in the field of stent delivery systems. More specifically, the materials which can be adopted for the balloon 13 include polyamide resins such as homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanic acid copolymer (nylon 6/11), caprolactam/ω-aminononane acid copolymer (nylon 6/9), caprolactam/hexamethylenediammonium adipate copolymer (nylon 6/66), adipic acid-methaxylenediamine copolymer, copolymers of hexamethylenediamine with m,p-phthalic acid, etc.; polyolefins such as polyalkylene resins such as polyethylene resins, e.g., linear low-density polyethylene (LLDPE), low-density polyethylene (LDPE), high-density polyethylene (HDPE), and polypropylene resins, etc., ethylene-propylene copolymer, ethylene-vinyl acetate copolymer, and their crosslinked products and partially crosslinked products (e.g., crosslinked ethylene-vinyl acetate copolymer), etc., epoxy resins, urethane resins, diallyl phthalate resins (allyl resins), polycarbonate resins, fluorine resins, amino resins (urea resin, melamine resin, benzoguanamine resin), polyester resins (e.g., polyethylene terephthalate), styrol resins, acrylic resins, polyacetal resins, vinyl acetate resins, phenolic resins, vinyl chloride resins, silicone resins (silicon resins), polyarylene sulfides (e.g., polyphenylene sulfide), silicone rubbers, latex rubbers, and nylon elastomers which are block copolymers of nylon 6, nylon 66, nylon 11, nylon 12 or the like as a hard segment with polyalkylene glycol, polyether, aliphatic polyester or the like as a soft segment.

These materials may be used either singly or in combination of two or more of them. In addition, the materials may be used in a monolayer form or a multilayer form. Besides, synthetic products of the above-mentioned polymeric materials may be used, and commercial products may also be used.

Now, dimensions of the components of the catheter 1 will be described. Since the catheter 1 is to be used in a method of treating sinusitis which will hereinafter be described, the dimensions of the components thereof are preferably in ranges suitable for insertion into the nasal cavity. More specifically, the whole length of the first elongated body 11 is preferably 50 to 3,000 mm. In addition, the outside diameter ("D1" in FIG. 4) of the first elongated body 11 is preferably 0.3 to 3 mm. Incidentally, the dimensions of the CCD camera

15 and the LED light 16 are appropriately determined according to the outside diameter ("D1" in FIG. 4) of the first elongated body 11.

Now, dimensions of the second elongated body 12 will be described. The whole length of the outer tube 121 (exclusive of the part inserted in the hub 14) of the second elongated body 12 is preferably 50 to 500 mm, and the length ("L1" in FIG. 2) from the distal end to the opening part 1210 of the outer tube 121 is preferably 20 to 30 mm. In addition, the outside diameter ("D3" in FIG. 4) of the outer tube 121 is preferably 1 to 5 mm, and the outside diameter ("D2" in FIG. 4) of the inner tube 122 is preferably 0.3 to 5 mm. The whole length of the parallel section 122a and the inclined section 122b of the inner tube 122 is appropriately determined according to the length ("L1" in FIG. 2) from the distal end to the opening part 1210 of the outer tube 121 and the whole length ("L3" in FIG. 2) of the balloon 13. Incidentally, the dimensions of the hub 14 are appropriately determined according to the dimensions of the second elongated body 12.

Now, dimensions of the balloon 13 will be described. The whole length ("L2" in FIG. 2) of the effective expansive section 13a of the balloon 13 is preferably sufficiently greater than approximately the whole length of a general stenosed part of a patient's natural ostium; specifically, it is preferably 5 to 30 mm. In addition, the whole length ("L3" in FIG. 2) of the balloon 13 inclusive of the tapered sections 13b1 and 13b2 is preferably 32 to 60 mm in the case where the whole length ("L2" in FIG. 2) of the effective expansive section 13a is 30 mm. Besides, the distance ("L4" in FIG. 2) from the image obtaining plane 15a of the CCD camera 15 to the distal end of the effective expansive section 13a is preferably 2 to 20 mm.

In addition, the outside diameter ("D4" in FIG. 4) of the balloon 13 before inflation is preferably set in the range of 0.3 to 5 mm, for ease of passage through the stenosed part of the natural ostium. Besides, the outside diameter ("D5" in FIG. 4) of the balloon 13 after inflation is preferably substantially equal to an ideal outside diameter of a communicating passage between the nasal cavity and the accessory nasal cavity that is to be formed in the natural ostium of a patient of sinusitis; specifically, it is preferably 2 to 10 mm.

Figure 6A:
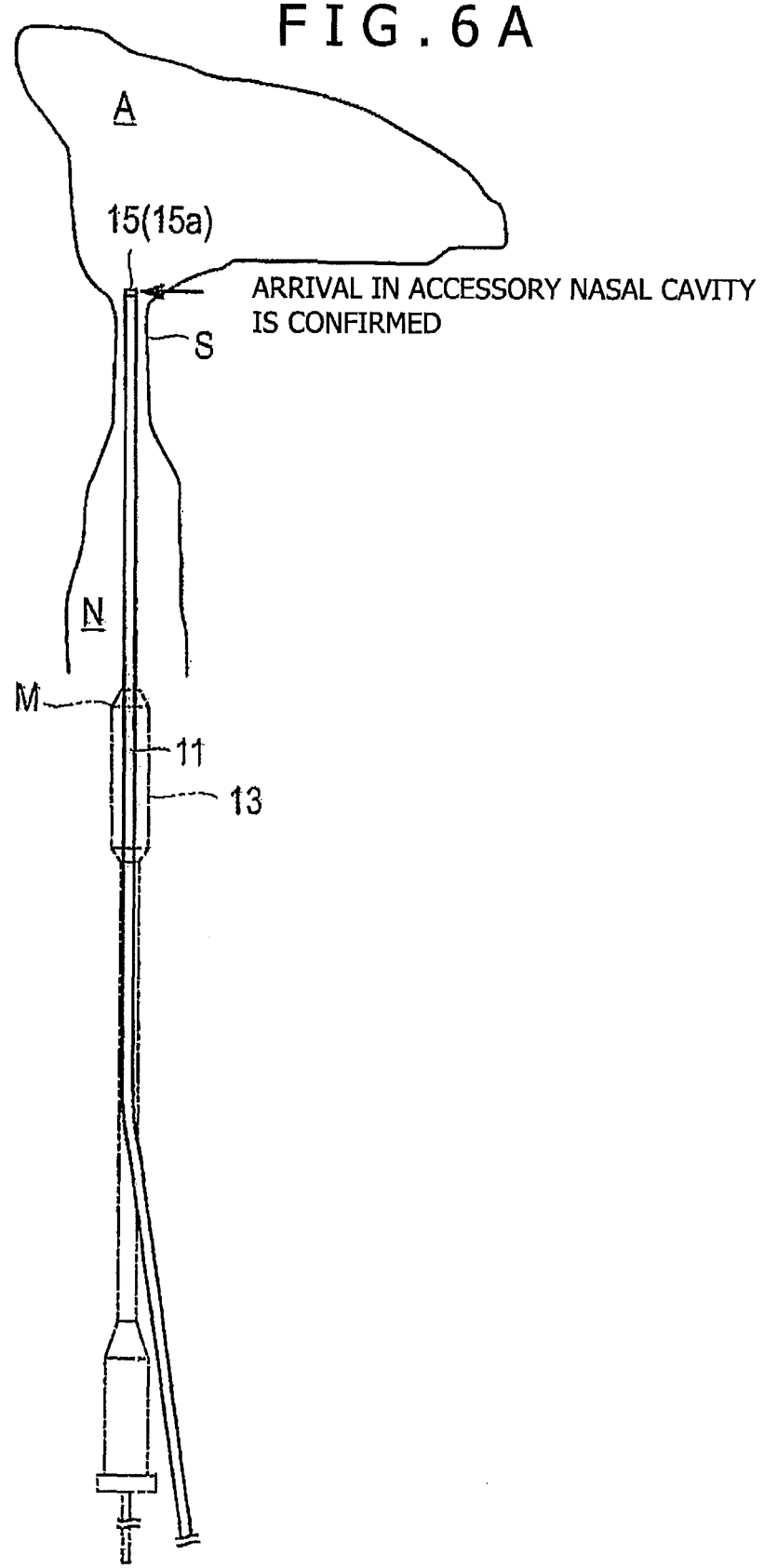
FIG. 6A is a schematic view showing a positioning method of a catheter according to one embodiment of the present invention.

Now, a method of positioning the balloon 13 by use of the marker M as a guide means in the present embodiment will be described below, referring to FIGS. 6A and 6B. First, in Step (1-1) the operator advances the first elongated body 11 (guide wire) into the nasal cavity N while watching the image obtained by the CCD camera 15 in the display device D, and stops the first elongated body 11 upon confirmation of the image of the inside of the accessory nasal cavity A on the display device D. By the Step (1-1), the CCD camera 15 can be passed through the stenosed part S of the natural ostium, and the image obtaining plane 15a is made to reach the entrance of the accessory nasal cavity A. FIG. 6A is a schematic view showing the positional relationship between the nasal cavity N and the first elongated body 11 (guide wire) upon completion of the Step (1-1).

Subsequently, in Step (1-2), the operator, in the state of holding the position of the first elongated body 11 (guide wire) in the nasal cavity N upon completion of the Step (1-1), advances the second elongated body 12 (catheter main body) within the nasal cavity N while watching the image obtained by the CCD camera 15 in the display device D. Then, in Step (1-3), the operator stops the second elongated body 12 (catheter main body) upon confirmation of the marker M in the display device D. This ensures that the distal end of the effective expansive section 13a can be delivered to the entrance of the accessory nasal cavity A. FIG. 6B is a schematic view showing the positional relationship between the nasal cavity N and the catheter 1 upon completion of the Step (1-3).

As shown in FIG. 6B, by the above-mentioned method, the effective expansive section 13a of the balloon 13 can be disposed over substantially the whole length of the stenosed part S, so that the whole of the stenosed part S can be pushed open upon inflation of the balloon 13. According to this method, therefore, the stenosed part S of the natural ostium can be pushed open more assuredly, so that a therapeutic effect on sinusitis can be enhanced. In addition, according to this method, the catheter 1 can be effectively prevented from being advanced excessively into the accessory nasal cavity, so that safety in treatment of sinusitis can be enhanced.

Now, a catheter 2 as a treatment device according to a second embodiment of the present invention will be described below. Like the catheter 1 according to the first embodiment as above-described, the catheter 2 in this embodiment includes a first elongated body 21 as a guide wire, a second elongated body 22 as a catheter main body, a balloon 23 as an expansion body for pushing open a stenosed part of the natural ostium in a nasal cavity, and a hub 24 as a proximal operating section to be operated by the operator. The first elongated body 21 is fitted with a CCD camera 25 as an imaging unit for obtaining an image of the inside of the nasal cavity, and an LED light 26 as an lighting unit for illuminating the inside of the nasal cavity so as to secure a visual field for the CCD camera 25. The structures of the components of the catheter 2 are the same as those in the above-described first embodiment, unless otherwise specified below.

FIG. 7A is an enlarged longitudinal sectional view showing the vicinity of the balloon 23 according to the present embodiment. As shown in FIG. 7A, the first elongated body 21 is positioned at an outer circumferential surface thereof with an enlarged diameter section 21e formed by partially enlarging the diameter in the radial direction. In addition, a positioning unit for positioning the balloon 23 (effective expansive section 23a) relative to the first elongated body 21 is disposed on the second elongated body 22. More specifically, the positioning unit in the present embodiment is a contact section 222r, which is formed by partially reducing the diameter of an inner circumferential surface of the parallel section 222a in the radial direction so as to make contact with the enlarged diameter section 21e when moved along the first elongated body 21.

As shown in FIG. 7A, the enlarged diameter section 21e and the contact section 222r are preferably so arranged that when they make contact with each other, the positions of the effective expansive section 23a and an image obtaining plane 25a projected onto the X-axis coincide with each other, and more preferably the positions of the distal end of the effective expansive section 23a and the image obtaining plane 25a projected onto the X-axis coincide with each other. In the example shown in FIG. 7A, the enlarged diameter section 21e and the contact section 222r extend respectively over the whole circumferences of the outer circumferential surface of the first elongated body 21 and the inner circumferential surface of the parallel section 222a of the second elongated body 22. However, at least one of the enlarged diameter section 21e and the contact section 222r may extend over only a part of the whole circumference of the outer circumferential surface of the first elongated body 21 or the parallel section 222a of the second elongated body. In addition, the lengths in the X-axis direction of the enlarged diameter section 21e and the contact section 222r are also not restricted to those in the example shown in FIG. 7A.

FIG. 7B is a longitudinal sectional view showing a condition after the positional relationship between the first elongated body 21 and the second elongated body 22 in FIG. 7A is changed. As shown in FIG. 7B, the contact section 222r on the second elongated body 22 moved along the first elongated body 21 makes contact with the enlarged diameter section 21e on the first elongated body 21 when the position of the proximal end of the effective expansive section 23a projected onto the X-axis and the position of the image obtaining plane 25a projected onto the X-axis coincide with each other. As a result, further movement of the second elongated body 22 is inhibited, so that the position of the proximal end of the effective expansive section 23a projected onto the X-axis and the position of the image obtaining plane 25a of the CCD camera 25 projected onto the X-axis can be made to coincide with each other as shown in FIG. 7B. This point will be further described later.

Now, a method of positioning the balloon 23 by use of the contact section 222c as a positioning unit according to the present embodiment will be described below, referring to FIGS. 6A and 6B. First, in Step (2-1), the operator advances the first elongated body 21 (guide wire) into the nasal cavity N while watching the image obtained by the CCD camera 25 in the display device D, and stops the first elongated body 21 upon confirmation of the image of the inside of the accessory nasal cavity A on the display device D. By this step, the CCD camera 25 can be passed through a stenosed part S of the natural ostium to cause the image obtaining plane 25a to reach the entrance of the accessory nasal cavity A. FIG. 6A is a schematic view showing the positional relationship between the nasal cavity N and the first elongated body 21 (guide wire) upon completion of the above-mentioned Step (2-1).

Subsequently, in Step (2-2), the operator, in the condition where the position of the first elongated body 21 (guide wire) in the nasal cavity N upon completion of the Step (2-1) is maintained, advances the second elongated body 22 (catheter main body) within the nasal cavity N until the contact section 222r on the second elongated body 22 (catheter main body) makes contact with the enlarged diameter section 21e on the first elongated body 21 (guide wire). FIG. 6B is a schematic view showing the positional relationship between the nasal cavity N and the catheter 2 upon completion of the above-mentioned Step (2-2).

As shown in FIG. 6B, it is possible by the above-mentioned method to arrange the effective expansive section 23a of the balloon 23 over substantially the whole length of the stenosed part S, so that the whole of the stenosed part S can be pushed open upon inflation of the balloon 23. According to the method, therefore, the stenosed part S of the natural ostium can be pushed open more assuredly, so that a therapeutic effect on sinusitis can be enhanced. In addition, according to the method, the catheter 2 can be effectively prevented from being advanced excessively into the accessory nasal cavity A, so that safety in treatment of sinusitis can be enhanced.

<Method of Treating Sinusitis by Use of Treatment Device According to the Present Invention>

As above-mentioned, the treatment device according to the present invention can be suitably used for treatment of sinusitis. Here, the form of use of the treatment device of the present invention for treatment of sinusitis is not specifically restricted. For example, the first elongated body is inserted into the nasal cavity; then, upon confirmation of the entrance of the accessory nasal cavity through the imaging unit positioned at the distal side, the second elongated body is introduced into the nasal cavity through use of the first elongated body; and, upon confirmation of a predetermined position, the expansion body is expanded, to dilate the stenosed part of the accessory nasal cavity. Thus, the present invention provides a method of treating sinusitis, including the steps of: (i) introducing a flexible first elongated body provided with an imaging unit into a nasal cavity; (ii) confirming the entrance of an accessory nasal cavity on the basis of an image obtained by the imaging unit; (iii) inserting the first elongated body in the lumen of a flexible second elongated body provided with an expansion body and introducing the second elongated body into the nasal cavity; and (iv) positioning an effective expansive section of the expansion body in a stenosed part of a natural ostium located between the nasal cavity and the accessory nasal cavity by a guide section (a positioning unit) provided on the second elongated body, for positioning the effective expansive section, and thereafter expanding the expansion body. Incidentally, the term "accessory nasal cavity" used herein may be any of frontal sinus, ethmoidal sinus, sphenoidal sinus, and maxillary sinus.

According to the above-mentioned method, the expansion body inside the nasal cavity can be positioned easily and accurately and the stenosed part of the accessory nasal cavity can be dilated assuredly and easily, by use of a simple device such as an endoscope, without using any special apparatus such as an X-ray apparatus. In addition, the method according to the present invention is a minimally invasive method based on the use of a catheter, which promises less-invasiveness to the patient.

Hereafter, a preferred embodiment of the method of treating sinusitis by use of the treatment device according to the present invention will be described, referring to the drawings. Incidentally, the invention is not to be restricted to the following embodiment.

Figure 8A:
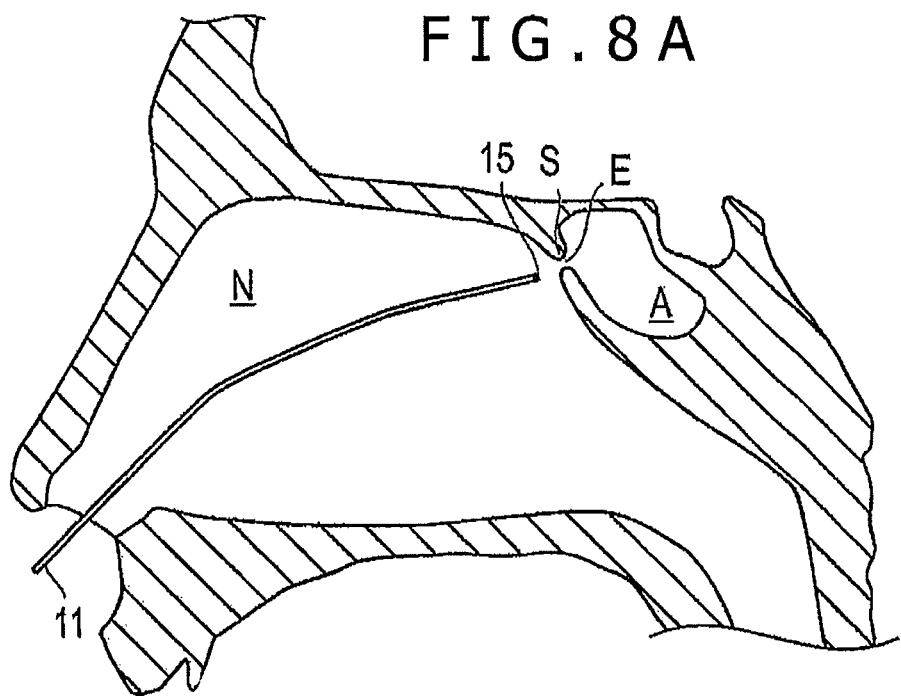
FIG. 8A is a schematic view showing a sinusitis treatment method using a treatment device according to one embodiment of the present invention.

First, the first elongated body 11 (in the second embodiment, the first elongated body 21; the same applies hereafter) is advanced from the naris through the nasal cavity N into the vicinity of the entrance E of the accessory nasal cavity A (e.g., sphenoidal sinus) (FIG. 8A). Next, the entrance E of the accessory nasal cavity A is confirmed based on the image obtained by the imaging unit 15, and, upon confirmation of the entrance E, the advancing of the first elongated body 11 is stopped and the first elongated body is tentatively disposed (FIG. 8B). Here, the position of the first elongated body 11 can be confirmed through the imaging unit 15.

For instance, the confirmation of the entrance E of the accessory nasal cavity A is carried out by confirming that the imaging unit 15 has been advanced into the accessory nasal cavity A, based on the image obtained by the imaging unit 15. More specifically, as shown in FIG. 8A, the first elongated body 11 is advanced into the nasal cavity N while watching the image obtained by the CCD camera 15 in the display device D, and the image of the inside of the accessory nasal cavity A is confirmed on the display device D. By this step, the CCD camera 15 can be passed through the stenosed part S of the natural ostium, and the image obtaining plane 15a can be delivered to the entrance E of the accessory nasal cavity A. When it is confirmed on the display device D that the first elongated body 11 has reached the entrance E of the accessory nasal cavity A, the first elongated body 11 is preferably fixed at the position upon the confirmation.

Figure 9A:
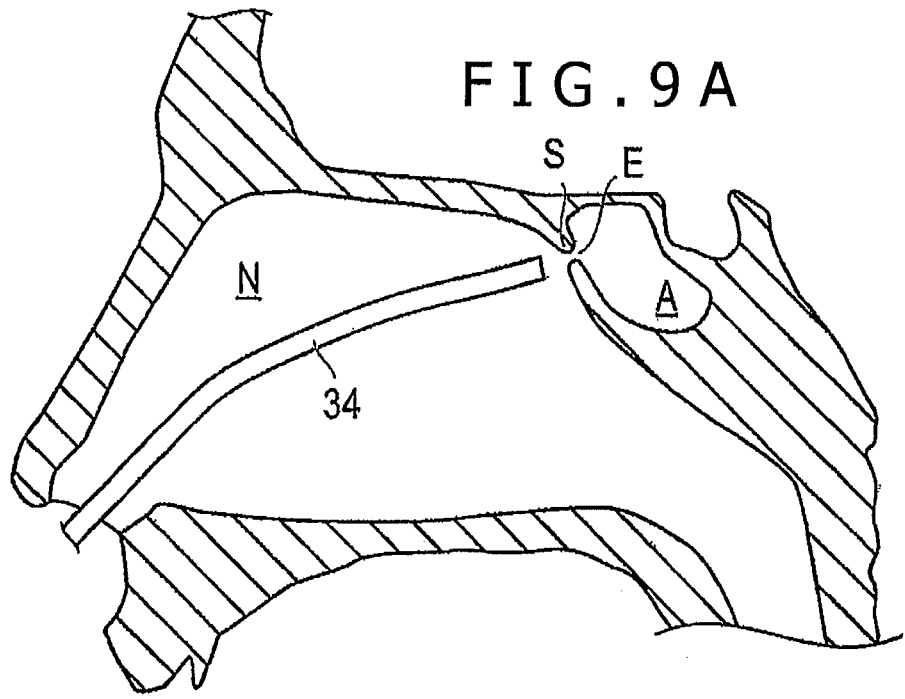
FIG. 9A is a schematic view showing another sinusitis treatment method using the treatment device according to the embodiment of FIGS. 8A to 8E.
Figure 9B:
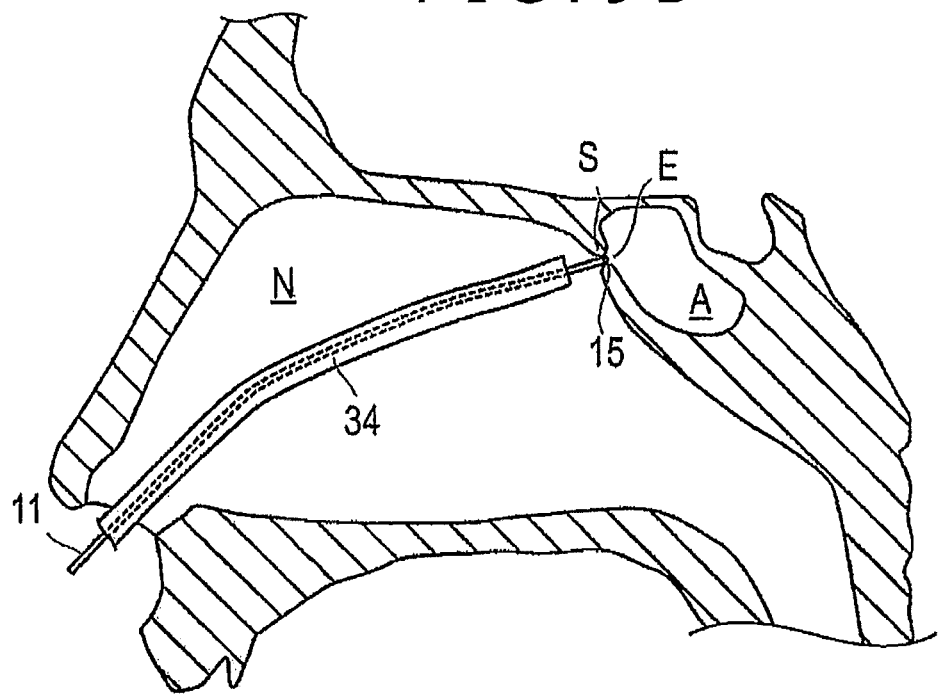
FIG. 9B is a schematic view showing another sinusitis treatment method using the treatment device according to the embodiment of FIGS. 8A to 8E.

Incidentally, in the present invention, the first elongated body 11 may be advanced directly from the naris through the nasal cavity N into the vicinity of the entrance E of the accessory nasal cavity A, as above-mentioned. Alternatively, the first elongated body 11 may be disposed into the vicinity of the entrance E of the accessory nasal cavity A by use of an assisting device such as a guide catheter. In that case, for example, as shown in FIG. 9A, first, a guide catheter 34 is inserted via the naris, and is advanced through the nasal cavity N into the vicinity of the entrance E of the accessory nasal cavity A (e.g., sphenoidal sinus) (FIG. 9A). After the guide catheter 34 is thus advanced to an appropriate position, the first elongated body 11 may be advanced through the guide catheter 34 into the vicinity of the entrance E of the accessory nasal cavity A (FIG. 9B). Here, the guide catheter is not specifically restricted, and guide catheters the same as or similar to those ordinarily used in the medical fields can be used in a similar manner; in consideration of operability and less-invasiveness to the nasal cavity, however, a flexible guide catheter is preferably used. Specific examples of the material which can be used to form the guide catheter include polymers such as polyimides, polyurethane, nylon, polyvinyl chloride (PVC), high-density polyethylene (HDPE), polyether ether ketone (PEEK), etc.; fluorinated polymers such as polytetrafluoroethylene (PTFE), tetrafluoroethylene-perfluoroalkyl vinyl ether copolymer (PFA), tetrafluoroethylene-hexafluoropropylene copolymer (FEP), tetrafluoroethylene-ethylene copolymer (ETFE); and metals such as stainless steel, etc. In addition, the diametral size (thickness) and the length of the guide catheter are not specifically restricted but may be appropriately selected according to the patient's weight and body type. The surface of the guide catheter may be coated with an appropriate coating film, such as a surface lubricating coating film for favorable sliding thereof.

Figure 8C:
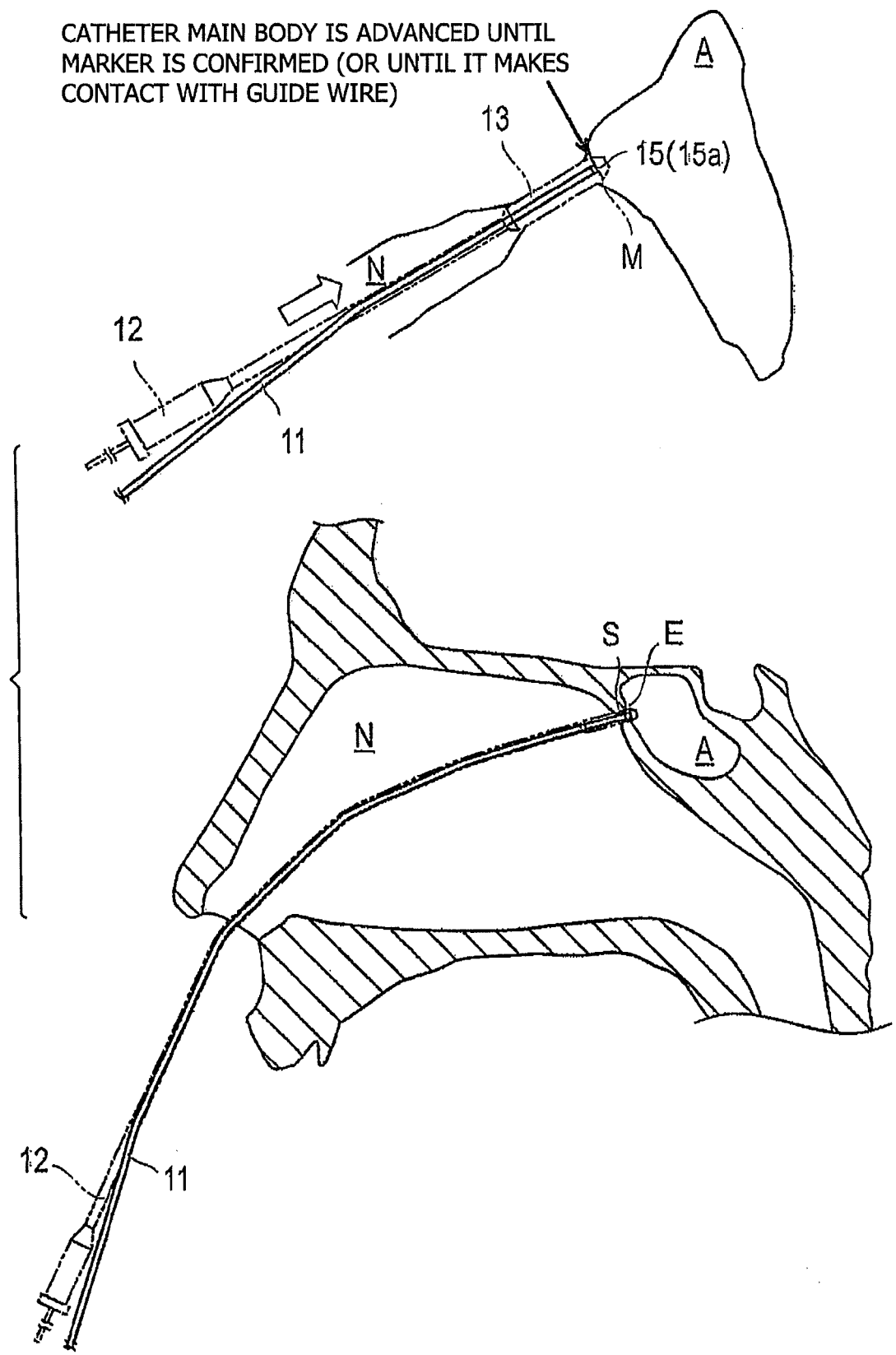
FIG. 8C is a schematic view showing a sinusitis treatment method using a treatment device according to one embodiment of the present invention.

Next, after the arrival of the first elongated body 11 in the entrance E of the accessory nasal cavity A is confirmed on the display device D, in the condition where the position of the first elongated body 11 in the nasal cavity N is maintained, the second elongated body 12 (in the second embodiment, the second elongated body 22; the same applies hereafter) is advanced through the first elongated body 11 in the nasal cavity N while watching the image obtained by the CCD camera 15 in the display device D (FIG. 8C). Here, in the case where the second elongated body 12 shown in FIGS. 5A and 5B which serves as the treatment device according to the first embodiment of the present invention is used, the advancing of the second elongated body 12 is stopped when the marker M is confirmed on the display device D through the function of the CCD camera 15 disposed at the distal end of the first elongated body 11, as shown in FIGS. 6A and 6B. By this step, the distal end of the effective expansive section 13a can be delivered to the entrance E of the accessory nasal cavity A. Besides, in the case where the second elongated body 22 shown in FIGS. 7A and 7B which serves as the treatment device according to the second embodiment of the present invention is used, the second elongated body 22 is advanced into the nasal cavity N until the contact section 222r on the second elongated body 22 makes contact with the enlarged diameter section 21e of the first elongated body 21, in the condition where the position of the first elongated body 21 in the nasal cavity N is maintained, after the arrival of the first elongated body 21 in the entrance E of the accessory nasal cavity A is confirmed on the display device D, as shown in FIGS. 6A and 6B. By this step, the distal end of the effective expansive section 23a can be made to reach the entrance E of the accessory nasal cavity A.

In the present embodiment, the advancing of the second elongated body 12 through the first elongated body 11 beyond the stenosed part S into the vicinity of the entrance E of the accessory nasal cavity A can be carried out while expanding the expansion body 13. This ensures that the catheter 1 is advanced while pushing open the stenosed part S, so that the stenosed part S can be dilated more assuredly.

After the distal end of the effective expansive section 13a of the expansion body (balloon) 13 is made to reach the entrance E of the accessory nasal cavity A by the above-mentioned operation, the stenosed part S of the natural ostium located between the nasal cavity N and the accessory nasal cavity A is dilated (FIG. 8D). Here, the expansion of the expansion body 13 may be conducted by use of a media, which may be the same or equivalent to those ordinarily used in the medical fields can be used. Specific examples of the medium which can be used here include gases such as air, nitrogen, carbon dioxide, etc.; and liquids such as physiological saline, radiopaque material, etc. In addition, the amount of the medium injected into the expansion body 13 is not specifically restricted but may be appropriately selected according to the stenosed part S (the inside diameter of the natural ostium), the inside diameter of the natural ostium after dilation, etc.

In the expanding (dilating) step, the expansion of the expansion body 13 may be carried out in any condition. For example, the expansion may be conducted in the state where the position of the second elongated body 12 is fixed, or may be conducted while advancing or retreating the second elongated body 12. In the former case, the stenosed part S is pushed open with a greater force, so that speedy and assured expansion can be achieved. In the latter case, on the other hand, the second elongated body 12 can be advanced or retreated while dilating the stenosed part S, so that this step can be applied particularly suitably to the case where the stenosed part S is quite narrow. After the stenosed part S can be dilated by the expanding step, the first elongated body 11 and the second elongated body 12 are pulled out. In this instance, the first elongated body 11 and the second elongated body 12 are preferably pulled out while confirming if the stenosed part S has been dilated, based on the image obtained by the imaging unit 15. This makes it possible to visually confirm that the stenosed part S has been dilated assuredly. In addition, the pulling-out of the first elongated body 11 and the second elongated body 12 can be carried out in any condition. For instance, the pulling-out is preferably conducted in the state where the expansion body 13 on the second elongated body is contracted, or while expanding the expansion body 13, or using an appropriate combination of the above-mentioned forms. This ensures that more assured dilation can be achieved.

Figure 8E:
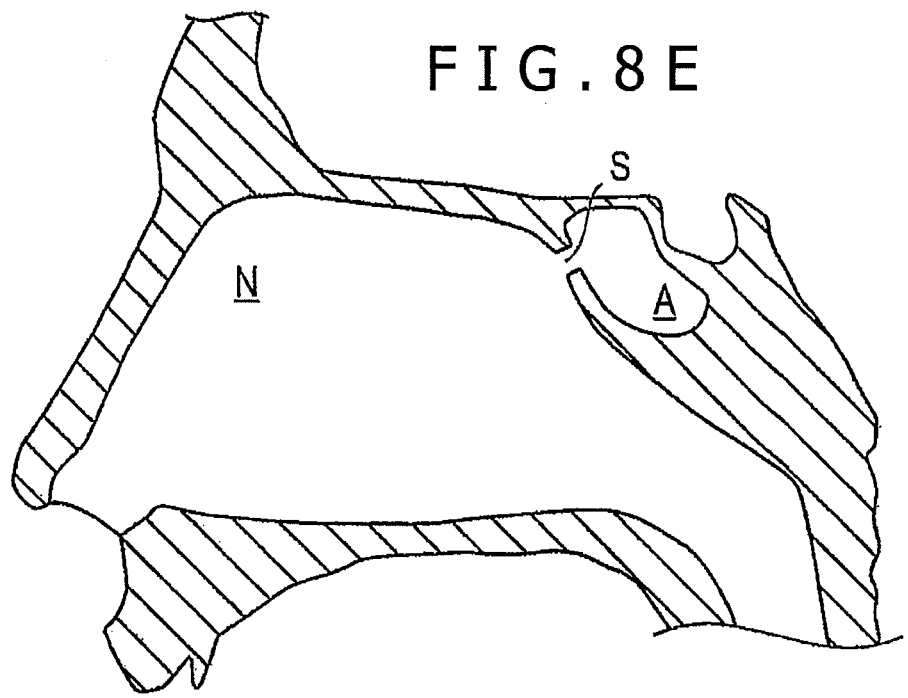
FIG. 8E is a schematic view showing a sinusitis treatment method using a treatment device according to one embodiment of the present invention.

When the first elongated body 11 and the second elongated body 12 are pulled out after the expanding step, the stenosed part S of the natural ostium located between the nasal cavity N and the accessory nasal cavity A is left in a dilated state (FIG. 8E).

According to the method of the present invention as above-described, the expansion body (balloon), particularly the effective expansive section of the expansion body (balloon) can be disposed over substantially the whole length of the stenosed part, so that the whole of the stenosed part can be pushed open when the expansion body (balloon) is expanded. According to the above-mentioned method, therefore, the stenosed part of the natural ostium can be pushed open more assuredly, so that a therapeutic effect on sinusitis can be enhanced. Besides, according to the above-described method, the catheter can be effectively prevented from being advanced excessively into the accessory nasal cavity, so that safety in treatment of sinusitis can be enhanced. Furthermore, according to the method of the present invention, the expansion body in the inside of the nasal cavity can be positioned easily and accurately, and the stenosed part of the accessory nasal cavity can be dilated assuredly and easily, by use of a simple device such as an endoscope, without using any special apparatus such as an X-ray apparatus. In addition, the method according to the present invention is a minimally invasive method based on the use of a catheter, which promises less-invasiveness to the patient.

The present invention may be practiced or embodied in still other ways without departing from the spirit or essential character thereof. The preferred embodiments described herein are therefore illustrative and not restrictive, the scope of the invention being indicated by the appended claims and all variations which fall within the meaning of the claims are intended to be embraced therein.

What is claimed is:

1. An otorhinolaryngological treatment device comprising:
    a flexible first elongated body;
    an image unit which is provided on the first elongated body, for obtaining an image on the front side of a distal end of the first elongated body;
    a flexible second elongated body having a lumen in which the first elongated body is inserted;
    an expansive body which is provided on the second elongated body and has an effective expansive section capable of radial expansive deformation within a natural ostium located between a nasal cavity and an accessory nasal cavity to push open a stenosed part of the natural ostium; and
    a positioning unit which is provided on the second elongated body, for positioning the effective expansive section of the second elongated body moved along the first elongated body relative to the first elongated body;
    wherein the positioning unit has a marker which is disposed on an inner circumferential surface of the lumen of the second elongated body and which can be visually confirmed in the image obtained by the imaging unit; and
    wherein, in a first state, positions of a distal end of the effective expansive section and the marker projected onto an extension axis of the second elongated body coincide with each other; and
    wherein, in a second state, the marker is disposed spaced a distance apart from a distal end of the second elongated body, said distance being a length from the distal end of the second elongated body to the distal end of the effective expansive section.

2. The treatment device according to claim 1, wherein the marker is a recess or projection which is disposed on the second elongated body.

3. The treatment device according to claim 1, wherein the marker is a boundary line between different colors on the second elongated body.

4. The treatment device according to claim 1, wherein the imaging unit is positioned at a distal end of the first elongated body.

5. An otorhinolaryngological treatment device comprising:
    a flexible first elongated body;
    an imaging unit which is provided on the first elongated body, for obtaining an image on the front side of a distal end of the first elongated body;
    a flexible second elongated body having a lumen in which the first elongated body is inserted;
    an expansive body which is provided on the second elongated body and has an effective expansive section capable of radial expansive deformation within a natural ostium located between a nasal cavity and an accessory nasal cavity to push open a stenosed part of the natural ostium; and
    a positioning unit which is provided on the second elongated body, for positioning the effective expansive section of the second elongated body moved along the first elongated body relative to the first elongated body;
    wherein the positioning unit has a contact section which is disposed on the inner circumferential surface of the lumen and which makes contact with the first elongated body when the second elongated body moves along the first elongated body;
    wherein the first elongated body has an enlarged diameter section which is partially enlarged in a radial direction;
    wherein the contact section is formed by partially reducing a diameter of the inner circumferential surface of the lumen in the radial direction so as to make contact with the enlarged diameter section of the first elongated body when moved along the first elongated body in an extension axis direction; and
    wherein the contact section is disposed on the inner circumferential surface of the lumen in such a manner that positions of the effective expansive section and an imaging obtaining plane of the imaging unit projected onto an extension axis of the second long body coincide with each other when the contact section makes contact with the first elongated body.

6. A method of dilating a stenosed part of a natural ostium of an accessory nasal cavity, comprising steps of:
    providing an otorhinolaryngological treatment device comprising a flexible first elongated body; an imaging unit which is provided on the first elongated body for obtaining an image on the front side of a distal end of the first elongated body; a flexible second elongated body having a lumen in which the first elongated body is inserted; an expansive body which is provided on the second elongated body and has an effective expansive section capable of radial expansive deformation within a natural ostium located between a nasal cavity and an accessory nasal cavity to push open a stenosed part of the natural ostium; and a positioning unit which is provided on the second elongated body for positioning the effective expansive section of the second elongated body moved along the first elongated body relative to the first elongated body;
    inserting the flexible first elongated body which is inserted in a lumen of a flexible second elongated body having an expansion body and which had an imaging unit, into the accessory nasal cavity on the basis of an image obtained by the imaging unit;
    advancing the second elongated body along the first elongated body to thereby introduce the second elongated body into the accessory nasal cavity;
    positioning and disposing the effective expansive section of the expansion body in the stenosed part by means of the positioning unit provided on the second elongated body; and
    expanding the expansion body to push open the stenosed part;
    wherein the positioning unit has a marker which is disposed on an inner circumferential surface of the lumen of the second elongated body and which can be visually confirmed in the image obtained by the imaging unit; and
    the step of disposing the effective expansive section in the stenosed part includes a step of confirming the position of the marker by means of the imaging unit.

7. The method of dilating a stenosed part according to claim 6,
    wherein the positioning unit has a contact section which is disposed on the inner circumferential surface of the lumen and which makes contact with the first elongated body when the second elongated body is moved along the first elongated; and the step of disposing the effective expansive section in the stenosed part includes a step of confirming the position of the contact section by bringing the contact section into contact with the first elongated body.

8. The method of dilating a stenosed part according to claim 6, wherein the step of pushing open the stenosed part includes a step of expanding and contracting the expansion body while advancing or retreating the second elongated body in a living body.

* * * * *